(12) United States Patent
Shinoki et al.

(10) Patent No.: US 6,287,785 B1
(45) Date of Patent: Sep. 11, 2001

(54) HOMOGENOUS ENZYME IMMUNOASSAY PROCESS

(75) Inventors: Hiroshi Shinoki; Osamu Seshimoto, both of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/488,371

(22) Filed: Jan. 20, 2000

(30) Foreign Application Priority Data

Jan. 22, 1999 (JP) ................................................ 11-14785

(51) Int. Cl.[7] .................................................. G01N 33/533
(52) U.S. Cl. ........................... 435/7.1; 435/7.6; 435/7.9; 435/7.91; 435/7.94; 435/7.92; 435/7.95; 435/174; 435/972; 435/963; 435/964; 435/969; 436/518; 436/537; 436/823; 436/538; 530/388.1; 530/391.1; 530/391.3; 530/866
(58) Field of Search .............................. 435/7.1, 7.6, 7.9, 435/7.91, 7.94, 7.92, 7.95, 174, 972, 963, 964, 969; 436/518, 537, 823, 538; 530/388.1, 391.1, 391.3, 866

(56) References Cited

U.S. PATENT DOCUMENTS

| | | | |
|---|---|---|---|
| 4,446,233 | * | 5/1984 | Auditore-Hargreaves et al. . |
| 4,481,298 | * | 11/1984 | Cone, Jr. et al. . |
| 4,692,404 | * | 9/1987 | Ashihara et al. . |
| 5,164,299 | * | 11/1992 | Lambert . |
| 5,415,998 | * | 5/1995 | Celada et al. . |
| 5,447,846 | * | 9/1995 | Shinoki et al. . |

FOREIGN PATENT DOCUMENTS

| | | | |
|---|---|---|---|
| 0579250 | * | 1/1994 | (EP) . |
| 0884591 | * | 12/1998 | (EP) . |

OTHER PUBLICATIONS

Rao et al., Journal of Immunoassay. 13(1):15–30, 1992.*

* cited by examiner

Primary Examiner—Jennifer Graser
(74) Attorney, Agent, or Firm—Reed Smith; Shaw & McClay LLP

(57) ABSTRACT

An improved homogeneous enzyme immunoassay process for quantitatively analyzing an antigen by determining the change in the enzymatic activity caused by a reaction between the antigen and an enzyme-labeled antibody. The antigen is reacted with an enzyme-labeled antibody, followed by the reaction with a second antibody capable of recognizing and binding to a different epitope and then with a third antibody capable of recognizing and binding to the second antibody. The enzymatic activity of the labeling enzyme is determined by a water-insoluble substrate. Using the water-insoluble substrate, steric hindrance is enhanced. A highly-sensitive analysis can be carried out by a simple operation even when the antigen has a molecular weight falling within an intermediate range, for example, a range of M.W. 10,000 to 70,000.

4 Claims, 1 Drawing Sheet

HOMOGENOUS ENZYME IMMUNOASSAY PROCESS

BACKGROUND OF THE INVENTION

1. Field of the Invention

The present invention relates to an immunoassay for quantitatively determining a trace constituent present in a sample, in which a reaction between an antigen and an antibody is utilized. More particularly, the present invention relates to a homogenous enzyme immunoassay for quantitatively determining an analyte antigen (ligand) in the sample by the use of an enzyme-labeled antibody.

2. Related Art

Analyses of the constituents originated from the living body or chemicals contained in the body fluids, such as blood or urine, are useful for diagnosing the condition of diseases or judging the course of curing, and thus they occupy important parts in the field of clinical test. The so-called enzyme immunoassay has been known in the art as one method for analyzing such constituents (ligands) generally present in a small amount in the body fluids. The enzyme immunoassay may be classified into a heterogeneous system for which B/F (Bound/Free) separation must be effected, and a homogeneous system in which B/F (Bound/Free) separation is not necessary. Meantime, B stands for the labeling material in a complex formed by binding of the specific antibody (or specific antigen) to the ligand, and F stands for the free labeling material which is not bound to the ligand.

In the heterogeneous system, the antigen-antibody bound (B) formed by the reaction between the antigen and antibody is separated from free antibody and antigen (F) by any suitable means and then the activity of the labeling enzyme in the antigen-antibody bound is determined. Although it is expected that the heterogeneous system has a high sensitivity in principle since the bound (B) is separated from free antibody and antigen (F), there is a problem that cumbersome operations are needed for the B/F separation and thus a relatively long time is necessary for the determination.

On the other hand, the reactions in the homogeneous system are based on the phenomenon that the enzymatic activity of the labeling enzyme is affected by some interference caused by binding of an antibody to the antigen (ligand), and the inhibition due to antigen-antibody binding is generally utilized. In general, the antigen is labeled with an enzyme so that the suppression in enzymatic activity either by a steric hindrance imposed on binding of the enzyme, which is bound to a generally large molecule antibody, with the substrate or by a change in three-dimensional structure of the enzyme is detected. For example, EMIT (Enzyme Multiplied Immunoassay Technique) is well known as such a system.

Alternatively, when the antigen is a high molecular weight substance, the antibody may be labeled with an enzyme and the suppression in enzymatic activity due to the antigen-antibody binding reaction may be utilized. The operations in the homogeneous system are thus relatively simplified since complicated B/F separation is not necessary. However, the homogeneous system has a disadvantage that the sensitivity thereof is lower in principle than that of the heterogeneous system.

Improved homegeneous immunoassaying processes for heightening the sensitivity have been disclosed in Unexamined Japanese Patent Publications (KOKAI) Nos. 108756/1985 (corresponding to U.S. Pat. No. 4,692,404), 295466/1991 (corresponding U.S. Pat. No. 5,569,598 and EP 0451848) and 128655/1992 (corresponding U.S. Ser. No. 08/946,685). In these prior-proposed processes, a water-insoluble high molecular weight substrate is used as the substrate for the enzyme. The enzymatic reaction takes place on the surface of the substrate particles which are giant molecules. As a result, the suppression in enzymatic activity due to steric hindrance caused by binding between the enzyme-labeled antibody and the antigen is exaggerated.

In the process disclosed in Unexamined Japanese Patent Publication No. 108756/1985 (U.S. Pat. No. 4,692,404), an antibody is subjected to a competitive reaction with an antigen (ligand) and an enzyme-labeled antigen, and the enzymatic activity of the labeling enzyme after the reaction is detected using an insoluble high molecular weight substrate.

The process described in Unexamined Japanese Patent Publication No. 295466/1991 (corresponding to U.S. Pat. No. 5,569,598) is for the assay of a high molecular weight antigen, in which the high molecular weight antigen (analyte) is reacted with an enzyme-labeled antibody. The enzyme of the enzyme-labeled antibody, which is bound to the high molecular weight antigen, cannot exhibit enzymatic activity on a water-insoluble substrate by steric hindrance. Accordingly, the quantity of enzymatic reaction products decreases with an increase in the quantity of the antigen to be analyzed.

The process described in Unexamined Japanese Patent Publication No. 128655/1992 is for the assay of a low molecular weight antigen, in which a polymerized antigen (i.e., a conjugate or linked product of the antigen (ligand) and a high molecular weight compound) is used. A competitive reaction is effected among the polymerized antigen, the antigen (analyte) and the enzyme-labeled antibody. In the enzyme-labeled antibody bound to the polymerized antigen, the enzymatic activity of the labeling enzyme to a water-insoluble substrate is interfered or hindered by steric hindrance. On the contrary, the enzyme of the enzyme-labeled antibody, which is combined with the antigen (ligand) contained in a sample, keeps its original enzymatic activity to the water-insoluble substrate. Accordingly, the quantity of the enzymatic reaction product increases in proportion to the quantity of the antigen in the sample.

In Unexamined Japanese Patent Publications Nos. 295466/1991 and 128655/1992, the sensitivity of the analysis is improved further by carrying out the above-described immunoreaction and enzymatic reaction in the layer construction of a dry immunoassay element. The immunoassay element has a reagent layer containing a fragmenting enzyme for further fragmenting the decomposition product produced by the labeling enzyme, so that the fragmented lower molecular weight product is detected for further sensitization of the element.

In the above-described manners, the quantities of high molecular weight and low molecular weight antigens (analytes) can be analyzed with a good sensitivity in accordance with the immunoassays described in Unexamined Japanese Patent Publications (KOKAI) Nos. 295466/1991 and 128655/1992, respectively.

When the molecular weight of the antigen falls within an intermediate range between those described in No. 295466/1991 and No. 128655/1992 of Unexamined Japanese Patent Publication, however, a sufficient sensitivity is sometimes unavailable by either of the above-described immunoassays.

In Unexamined Japanese Patent Publication No. 295466/1991, the difference in the enzymatic activity between an antigen-antibody-enzyme complex and an antibody-enzyme complex is detected. The antigen (analyte) is accordingly required to have such a molecular weight as to reveal an interference or inhibition to the enzymatic activity, when binding to the enzyme-labeled antibody. When an intact IgG molecule (M.W. ca. 160,000) is used as the antibody, the active site of the labeling enzyme has already been affected to some extent by the linkage with this IgG. For increasing the steric hindrance against the enzymatic activity by the binding of the antigen, the antigen (analyte) is required to have a molecular weight sufficient for the molecular weight of the antibody which has already be linked. Even if Fab or Fab' fragment (M.W. ca. 50,000) is employed as the antibody, the antigen (analyte) must have a molecular weight sufficient for it. It is considered to be possible to detect the difference in the enzymatic activity between the antigen-antibody-enzyme complex and the antibody-enzyme complex when the antigen has, for example, a molecular weight of 20,000 daltons or greater, preferably about 50,000 daltons or more. Even if the antigen has a molecular weight falling within the above-described range, however, the detection sensitivity lowers with a decrease in the molecular weight of the antigen.

When the antigen (analyte) has a small molecular weight, on the other hand, a polymerized antigen having an increased molecular weight is employed as described in Unexamined Japanese Patent Publication No. 128655/1992. In this case, detected is a difference in the enzymatic activity between the polymerized antigen-antibody-enzyme complex and the antigen (analyte)-antibody-enzyme complex. With an increase in the molecular weight of the antigen (analyte), the enzymatic activity exhibited by the antigen (analyte)-antibody-enzyme complex is suppressed, leading to a reduction in the difference with the enzymatic activity exhibited by the polymerized antigen-antibody-enzyme complex. This immunoassay system is applicable to the antigen (analyte) having a molecular weight of about 20,000 daltons or less, but the less the molecular weight of the antigen, the better the detection sensitivity. On the contrary, with an increase in the molecular weight of the antigen, the detection sensitivity lowers.

Thus, neither of the above-described immunoassay systems brings about sufficient detection sensitivity when an antigen (analyte) has an intermediate molecular weight, for example, within a range of 10,000 to 70,000.

OBJECTS AND SUMMARY OF THE INVENTION:

The present invention has been accomplished in view of the aforementioned circumstances, and an object thereof is to provide a homogeneous enzyme immunoassay process for enabling a highly sensitive analysis while using a simple operation even when an antigen to be analyzed has a molecular weight falling within an intermediate range.

The object of the present invention is attained by the provision of a homogeneous enzyme immunoassay process for quantitatively analyzing an antigen by determining the change in enzymatic activity caused by a reaction between said antigen and an enzyme-labeled antibody, said process comprising: providing said enzyme-labeled antibody being a conjugate of a labeling enzyme and a monoclonal first antibody; reacting said antigen with said enzyme-labeled antibody to obtain a first reaction mixture, said first antibody recognizing and binding to a first epitope of the antigen; reacting said first reaction mixture with a monoclonal second antibody capable of recognizing and binding to a second epitope of said antigen different from the first epitope to obtain a second reaction mixture; reacting said second reaction mixture with a third antibody capable of recognizing and binding to said second antibody to obtain a third reaction mixture; and determining the enzymatic activity of said labeling enzyme in said third reaction mixture from a water-insoluble substrate.

In the present invention, steric hindrance is enhanced by binding the antigen to the enzyme-labeled antibody, followed by successive binding to the second and third antibodies. The steric hindrance is eminent when the substrate for the enzyme is water insoluble. As is also apparent from Examples which will be described later, steric hindrance against enzymatic activity is hardly observed when a water-soluble substrate is employed. Although it has not been clarified why the steric hindrance to a water-insoluble substrate appears strongly by the use of the second and subsequent third antibodies, it is estimated that the steric hindrance appears strongly for the following reason.

When the enzyme-labeled antibody reacts with an analyte antigen, the active site of the labeling enzyme generally suffers steric hindrance by the antigen. For actually disturbing the approach of the substrate to the enzyme active site, the substrate must have a molecular weight large enough to be affected by the antigen. In other words, if the substrate for the enzyme has a certain molecular weight, it will suffer from steric hindrance by the antigen. In such a case, steric hindrance against the approach of the substrate to the enzyme active site is presumed to become more effective by the use of the second and third antibodies as in the present invention.

The water-soluble substrate generally has a low molecular weight so that it can easily approach to the enzyme active site. Some of high molecular weight substrates are however soluble in water. Such high molecular weight substrate is constituted of high polymer chains and has an intra-molecular action between the polymer chains, which strongly appears in the solid state. When the high polymer substrate is immersed in a solvent (water), molecules of the solvent enter between the high polymer chains and expands the substrate to form a gel. The high polymer chains surrounded by the solvent molecules are separated, dispersed in the solvent one by one and are finally dissolved therein. The water-soluble substrate is thus able to approach to the active site of the enzyme by the free movement of molecules in the solvent. The use of a water-soluble substrate is presumed to be the reason why no inhibition of enzymatic activity was recognized in the below-described Example 7 wherein second and third antibodies were used.

On the other hand, a water-insoluble substrate is generally a macromolecular having a large molecular weight. When a high molecular weight substance has a bonded structure (cross-linked structure) between some of high polymer chains, it is impossible to separate them. The water-insoluble substrate therefore swells in a solvent but is not soluble therein. Such an insoluble substrate reacts with an enzyme on the surface of its particles. Namely, the enzymatic reaction takes place at the solid-liquid interface, which increases the influence of the steric hindrance against the enzyme. In the present invention, with a view to allowing the steric hindrance to exhibit more easily, an antigen is reacted with an enzyme-labeled antibody, the reaction mixture is reacted with and bound to second and third antibodies and then the enzymatic activity is measured using an insoluble substrate.

In a preferred embodiment of the invention, IgG fragments such as Fab' and Fab may be used as an antibody of the enzyme-labeled antibody. These fragments are preferred because they have no Fc region which might cause noise. Fab' fragment is particularly preferred since it has free SH group at the hinge region of the antibody to facilitate binding with the used enzyme. As the second antibody, intact IgG may be used and as the third antibodyspecific binding to the Fc region of the second antibody may be used.

The enzymatic activity of the labeling enzyme in the reaction mixture can be determined by the addition of an insoluble substrate thereto. If necessary, it is possible to add a color-developing reagent composition to the enzymatic reaction product, thereby causing color development in proportion to the enzymatic activity and then to carry out colorimetric analysis. Alternatively, the enzymatic activity may be determined by a dry immunoassay element equipped with a substrate layer containing a water insoluble substrate.

DESCRIPTION OF PREFERRED EMBODIMENTS

Analyte (Substance to Be Analyzed)

Figure 1:
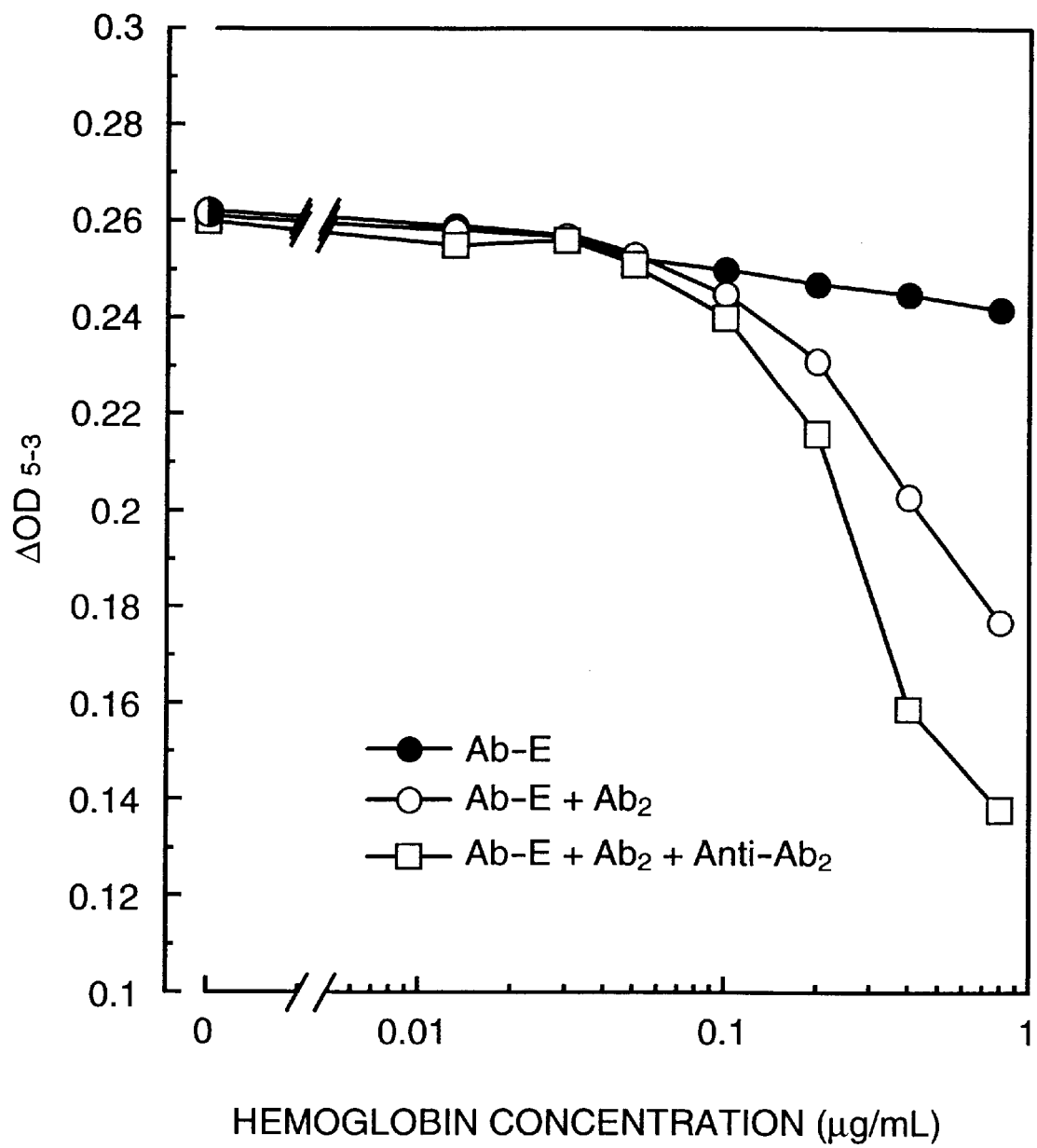
FIG. 1 illustrates calibration curves drawn as a result of the analysis in Example 6. In the drawing, the symbol -●- indicates the case where only an enzyme-labeled antibody was reacted with an antigen (Comparative Example 1), while the symbol -○- indicates the case where the enzyme-labeled antibody and second antibody were reacted with an antigen (Comparative Example 2). Each of them is provided as a control. The symbol -□- indicates the case where the enzyme-labeled antibody, second antibody and third antibody were reacted in this order with an antigen in accordance with the present invention.

The substance to be analyzed by the present invention (hereinafter referred to simply as "analyte") is a ligand having an antigenic determinant and contained in the sample, that is, an antigen. No limitation is imposed on the sample and many kinds of sample may be analyzed by this invention. Typical examples include blood (whole blood, blood plasma, blood serum), lymph fluid and urine. It suffices that the ligand is an antigen having two or more different epitopes (antigenic determinants). However, it is not necessary that structural features of these epitopes are made clear or identified. It suffices that at least two sorts of monoclonal antibodies, which are immunologically distinguishable from each other, can be obtained from them.

A ligand having any molecular weight, from a low molecular weight to a high molecular weight, can be analyzed by the immunoassay according to the present invention insofar as it has at least two epitopes. Medicaments or derivatives thereof having a low molecular weight are however excluded because they scarcely have two or more epitopes. When the antigen has a molecular weight high enough to inhibit the enzymatic activity of the enzyme-labeled antibody by binding thereto, it is not necessary to employ the second and third antibodies. Accordingly, the present invention can exhibit its advantage most effectively when the antigen has at least two epitopes and has a molecular weight within an extent not inhibiting the enzymatic activity of the enzyme-labeled antibody sufficiently when bound to the enzyme-labeled antibody. The preferred molecular weight range of the antigen differs with the antibody of the enzyme-labeled antibody (first antibody), whether it is IgG (M.W. ca. 160,000) or Fab' or Fab (each, M.W. ca. 50,000). When the first antibody is Fab' or Fab, the preferred molecular weight of the analyte antigen falls within a range of about 10,000 to 70,000, with a range of about 10,000 to 30,000 being most preferred.

Examples of such an antigen include polypeptide, low molecular weight protein and subunit of protein. For example, human hemoglobin (which has a molecular weight of about 64,000 and is composed of 4 subunits, one of the subunits having a molecular weight of about 16,000), HCG (human chorionic gonadotropin; M.W. ca. 37,000) or the like can be analyzed by the immunoassay of the present invention. In addition, TSH (thyroid-stimulating hormone; M.W. ca. 28,000), LH (luteinizing hormone; M.W. ca. 29,000), insulin (M.W. ca. 5,800), apoprotein A-I (M.W. ca. 28,000), apoprotein A-II (M.W. ca. 18,000), apoprotein C-II (M.W. ca. 8,500), apoprotein C-III (M.W. ca. 8,500), apoprotein E (M.W. ca. 36,000), AT III (angiotensin III; M.W. ca. 59,000), AFP (α-fetoprotein; M.W. ca. 68,000) and $\beta_2$-microglobulin (M.W. ca. 11,800).

Antibody

Two or more monoclonal antibodies capable of recognizing and binding to different epitopes of the same analyte antigen is used as the first and second antibodies.

The monoclonal antibodies may be obtained and prepared by the conventional method. In detail, the antigen is injected into the peritoneal cavity of an immuno-recipient animal (mouse) together with an adjuvant for several times. The spleen cells taken out from the recipient are fused with the murine myeloma cells using polyethylene glycol or the like. The fused cells are subjected to cloning to obtain antibody producing cells which are proliferated as the monoclonal cells. The thus proliferated cells are injected intraperitoneally to a mouse so as to obtain the ascites and the serum containing the monoclonal antibodies. The antibodies may be easily purified by the process in which ammonium sulfate precipitation, ion exchange chromatography, affinity chromatography (Protein-A agarose etc.) and gel filtration are combined as needed. The antibodies may be classified into sub-classes including IgG1, IgG2a and IgG2b, and the antibodies of IgG1 are particularly preferred since they are excellent in fragmenting efficiency at the step of preparing an enzyme-antibody complex. IgG1 may be digested by protease such as activated papain or pepsin, whereby the Fc region may be removed from intact IgG1 to prepare F(ab')$_2$ fragment. The prepared F(ab')$_2$ may be cleaved into Fab' fragment by the reduction of S-S linkage.

Selection of the monoclonal antibodies for the determination of different epitopes may be effected through the ELISA (enzyme-linked immunosorbent assay). For example, an antigen is bound to a micro-titer plate coated or sensitized with a monoclonal antibody 1, and then another biotinated monoclonal antibody 2, which is separately prepared, is reacted with the antigen. Additional binding of the biotinated monoclonal antibody 2 with the antigen is examined using avidin-POD (peroxidase). When the reaction is positive, it is judged that the antibody 1 and the antibody 2 recognize different epitopes. Thus, a combination of two monoclonal antibodies are respectively specific to two distinct epitopes of the antigen under investigation.

In a preferred embodiment of the invention, an Fab' fragment is used as the monoclonal first antibody. An intact antibody (IgG) has the Fab (antigen-binding region) and the Fc (complement fixing region). When an intact antibody is bound to an enzyme to be used for the enzyme-labeled antibody in the analysis of a blood sample, the complement constituents contained in the blood sample tend to bind to the Fc region to cause steric hindrance, thereby inhibiting the enzymatic activity. Even if the sample is not blood, non-specific adsorption is resulted by the presence of Fc region, leading to the result that the antibodies are adsorbed to the wall of the used reaction vessel, whereby the apparent activity of the enzyme-labeled antibody is lowered to cause noise in the determination step. It is thus desirous to use Fab', F(ab')$_2$ or Fab fragments containing no Fc region as the antibody in order to exclude such noise. The most preferable first antibody is an Fab' fragment containing a free SH group from the viewpoint of easy linkage with an enzyme.

No such limitation is imposed on the second antibody. Even intact antibody (IgG) can be used as the second antibody. Since IgG contains an Fc region, the use of IgG as the second body is rather preferable, which makes it possible to employ an anti-Fc antibody as the third antibody.

The third antibody is an antibody for recognizing and binding to the second antibody. Either a monoclonal antibody or a polyclonal antibody may be employed. When the second antibody (monoclonal antibody) is obtained from a mouse, an anti-mouse IgG antibody may be used as the third antibody. As such a third antibody, usable are polyclonal antibodies available by immunizing, with the second antibody, an animal (goat, sheep, rabbit or the like) other than mouse. When the second antibody is an intact mouse IgG, a commercially available anti-mouse Fc antibody may be used as the third antibody.

Labeling Enzyme

The enzyme for forming the enzyme-antibody complex can be selected in consideration of the combination with the substrate which is used at the subsequent enzymatic reaction and a detection system of the enzymatic reaction product. In the present invention, since the reactivity of the enzyme with the substrate is suppressed by the steric hindrance resulted from the formation of an enzyme-antibody-antigen-second antibody-third antibody complex, it is preferred to select a combination of the enzyme and the substrate from which influence by the steric hindrance is easily detected. In short, a substrate having a relatively high molecular weight is preferred for attaining a higher sensitivity. For example, a substrate having a molecular weight of not less than about 20,000, preferably not less than about 100,000 is used in the invention. Examples of such substrates include a starch as the substrate for an enzyme amylase; a cellulose as the substrate for an enzyme cellulase; proteins such as gelatin and hemocyanin as the substrate for protease; and various oils and fats as the substrate for lipase. Detailed reports relating to the selection of the enzymes and substrates are disclosed in Unexamined Japanese Patent Publication Nos. 108756/1985 (corresponding to U.S. Pat. No. 4,692,404 and EP 0144176A), 171461/1985 (corresponding U.S. Pat. No. 4,757,001 and EP 0152305A) and 171460/1985 (corresponding U.S. Pat. No. 4,757,001 and EP 0152305A). Amylase used with starch as the substrate is preferred. It is particularly preferred that the substrate is a water-insoluble substrate, since the steric hindrance by the presence of the enzyme-antibody-antigen matrix structure is noticeably appeared. Examples of such an enzyme include a hydrolase which a forms a diffusible oligomer from a non-diffusible (water insoluble) substrate composed of polymers, specific example being glucosidase. Examples of glucosidases include endo-active glucosidases such as α-amylase, β-amylase and dextranase.

Water-Insoluble Substrate

When an α-amylase is used as the labeling enzyme, carboxymethylated starch, starch, amylose, amylopectin or the like may be used as the substrate. It is particularly preferred for the improvement in sensitivity to use water-insoluble starch, since the enzymatic reaction takes place on the surfaces of the substrate particles, namely the reaction takes place at the solid-liquid interface to exaggerate the influence of steric hindrance to the enzymatic activity by the occurrence of antigen-antibody binding. Alternatively, a water-insoluble dye-starch may be used, followed by detection of the dye bound to the soluble amylose which is the decomposition product of enzymatic reaction. An example of commercially available water-insoluble blue starch polymer is Neoamylase test "Dai-ichi" (produced by Daiichi Pure Chemicals, Co., Ltd.).

Linking between Enzyme and Antibody

The enzyme may be linked with the antibody while utilizing the functional groups (amino, carboxyl, thiol, etc.) of these two substances. Representative linking methods include glutaraldehyde method, the periodic acid method, the pyridyl-disulfide method, and the maleimide-succinimide method. The linking method is not limited only to the representative methods as described above, and may be selected as needed from the methods described in "Method in Immunology and Immunochemistry", Vol. 1, (C. A. Williams, M. W. Chase, Academic Press (1967)) or "KOSO MEN'EKI SOKUTEI-HO (Enzyme immunoassay)", edited by Ishikawa, Kawai and Miyai, published by Igaku Shoin in 1978. The maleimide-succinimide method, in which a thiol group at the hinge region of the antibody is linked with an amino group of the enzyme, is preferred since it is excellent in reaction efficiency while retaining the activity of the antibody.

In the maleimide-succinimide method, the enzyme is linked with Fab', for example, through the following steps. Initially, amino groups of the enzyme are maleimidated by a maleimide-succinimide reagent. The reaction product is subjected to gel filtration for purification, and then subjected to the reaction for forming a conjugate with the antibody (Fab') having thiol groups. The molar ratio of the enzyme to the antibody in the conjugate-forming reaction preferably ranges from 1:3 to 1:7. For example, when a Fab' (having a molecular weight of about 50,000) is used as the antibody and an α-amylase (having a molecular weight of about 50,000) is used as the enzyme, the preferable weight ratio of the α-amylase to the Fab' ranges from 1/3 to 1/7. This linking reaction proceeds generally at 4° C. to room temperature.

The thus prepared enzyme-antibody complex (enzyme-labeled antibody) is purified through gel filtration, and dried through lyophilization as desired. The ratio between the enzyme and the monoclonal antibody in the linked product is not limited to 1:1, but may be changed to a desired ratio in consideration of the applied use of the product. In general, since the enzyme has plural amino groups, plural maleimide groups are introduced and linked with plural antibody molecules. The molar ratio of the antibody to the enzyme in the produced complex preferably falls within a range of from 4 to 5 in order to ensure high detection sensitivity. When the Fab' fragment (having a molecular weight of about 50,000) is used as the antibody and an α-amylase (having a molecular weight of about 50,000) is used as the enzyme, the preferable molecular weight of the enzyme-antibody complex ranges from 150,000 daltons, more preferably from 250,000 to 300,000 daltons, to ensure high detection sensitivity.

Assaying process

The analyte antigen contained in the sample is allowed to contact with the enzyme-antibody complex in a solution, followed by the successive addition of the second antibody (a monoclonal antibody which is capable of recognizing and binding to an epitope of the antigen different from another epitope of the same antigen recognizable by the first antibody) and the third antibody (capable of recognizing and binding to the second antibody). It is preferred that the temperature of the solution ranges from about 20° C. to 45°

C., and the pH value of the solution ranges from about 4.0 to about 8.5. A buffer such as phosphate buffer or acetate buffer may be used to maintain the pH value of the solution at the constant level. The time for allowing the antigen to contact with the enzyme-antibody complex may be determined to ensure complete reaction, for example, ranging from 20 to 30 minutes when the temperature of the solution is 37° C. The reaction time with the second antibody or the third antibody may be determined to ensure complete reaction, for example, 5 to 10 minutes when the temperature of the solution is 37° C. After the above-described a series of immunoreactions, a substrate for the enzyme is added to the solution, and the enzymatic activity of the labeling enzyme is measured. The presence of analyte antigen in the sample can be detected as the inhibition in enzymatic activity. By preparing a calibration curve drawn by using solutions each containing a known quantity of the analyte antigen, the analyte antigen contained in the sample can be quantitatively analyzed.

In an alternative embodiment, only a series of immunoreactions, that is, the reaction between the antigen and the enzyme-antibody complex and subsequent reactions with the second and third antibodies are performed in a solution system and then, the enzymatic activity of the reaction mixture may be analyzed using a dry system. In detail, a dry analysis element having a substrate layer containing the substrate for the labeling enzyme is prepared, and the reaction mixture after the completion of the immunoreactions is spotted on the dry analysis element to measure the enzymatic activity. Such a dry analysis element has the layer structure similar to that described in Unexamined Japanese Patent Publications Nos. 295466/1991, 128655/1992 and the like.

For example, when the labeling enzyme is α-amylase, a substrate layer containing carboxymethylated starch as an insoluble substrate is arranged as the uppermost layer of the dry analysis element. In a reagent layer disposed below the substrate layer, a fragmenting or digesting enzyme (e.g., glucoamylase) for further decomposing an oligomer, which is a decomposition product of the enzymatic reaction of carboxymethylated starch, into the corresponding monomer (glucose) is incorporated. The glucose can optically be detected by a detection reagent composition contained also in the reagent layer. As such a detection reagent composition, a combination of glucose oxidase, peroxidase and leuco dye may be employed.

EXAMPLE 1
Preparation of Anti-human Hemoglobin IgG

Each of two different monoclonal antibodies IgG against the human Hb (hemoglobin) was prepared through a conventional process in which immunized cells (spleen cells) obtained by the immunization of a mouse were fused with murine myeloma cells, followed by cloning process. The below-described Fab' fragment for the first antibody was prepared from one of the two different monoclonal antibodies, after confirming that each monoclonal antibody specifically recognizes different epitopes of the same antigen. The other monoclonal antibody (IgG) was used as the second antibody in the below-described Examples 6 and 7.

EXAMPLE 2
Preparation of Anti-Human Hb IgG Fab' (First Antibody)

4.4 mg of the first anti-human Hb antibody IgG was dissolved in 1 mL of a 0.1 M acetate buffer (pH 5.5) and then added with 132 μg of activated papain, followed by stirring the mixture at 37° C. for 2 hours. The reaction mixture was then applied to a SUPERDEX-200 gel column, which had been preliminarily equilibrated with a 0.1 M phosphate buffer (pH 6.0, containing 1 mM EDTA-2Na), followed by elution with the same phosphate buffer. The peak fraction of the eluate having a molecular weight of about 100,000 daltons was collected to obtain an anti-human Hb IgG F(ab')$_2$. 5 mL of 0.1 M phosphate buffer (pH 6.0) containing 2.2 mg of the thus prepared anti-human Hb IgG F(ab')$_2$ was added with 100 μL of a 113 mg/mL aqueous solution of 2-mercaptoethylamine-HCl salt to proceed the reaction at 37° C. for 2 hours with stirring. The reaction mixture was subjected to gel filtration by a SEPHADEX G-25, which had been preliminarily equilibrated with a 0.1 M glycerophosphate buffer (pH 7.0, containing 5 mM EDTA-Ca), to collect the passing fraction. The thus prepared anti-human Hb IgG Fab' (hereinafter referred to as "Fab'", simply) fraction was used as the first antibody to be labeled with a labeling enzyme.

EXAMPLE 3
Preparation of GMB Amylase:

Maleimide groups were introduced into α-amylase through the following processing steps. To 1 mL of a 10 mg/mL *Bacillus subtilis* α-amylase solution (in a 0.1 M glycero-phosphate buffer solution, pH 7.0), 100 μL of a 100 mg/mL solution of GMBS (N-(γ-maleimidobutyryloxy) succinimide; produced by DOJIN KAGAKU) in DMF was added and allowed to react at room temperature for 2 hours. The reaction mixture was subjected to the gel filtration through a SEPHADEX G-25 column, and the passing fraction was collected to obtain (N-(γ-maleimidobutyryloxy) amidated amylase (GMB amylase). The concentration of the thus obtained GMB amylase solution was 1.12 mg/mL.

EXAMPLE 4
Preparation of α-amylase/Fab' Bound 3.65 mL of 0.1 mg/mL solution of anti-human Hb IgG Fab' (Fab') prepared in Example 2 was added with 54 μL of the GMB amylase solution prepared in Example 3. The resulting mixture was maintained at 4° C. for 20 hours to proceed the reaction. The reaction mixture was then applied to a SUPERDEX-200, which had been preliminarily equilibrated with a 0.1 M glycerophosphate buffer (pH 7.0, containing 0.5 mM EDTA-Ca), to effect elution using the same glycerophosphate buffer. The peak fraction of the eluate having the molecular weight of about 270,000 daltons was collected to obtain an enzyme-labeled antibody (α-amylase/Fab' bound).

EXAMPLE 5
Preparation of Immunoassay Element for a-amylase

On a colorless and transparent polyethylene terephthalate (PET) sheet (support) coated with a gelatin undercoating layer and having a thickness of 180 μm, coated was a reagent solution containing a cross-linking reagent, followed by drying, to form a reagent layer so that respective components had the coverage as set forth below.

| | |
|---|---|
| Alkaline-treated Gelatin | 14.5 g/m$^2$ |
| Nonylphenoxypolyethoxyethanol | 0.2 g/m$^2$ |
| (Containing 9 to 10 oxyethylene units on average) | |
| Glucose Oxidase | 5,000 U/m$^2$ |
| Peroxidase | 15,000 U/m$^2$ |
| Glucoamylase | 5,000 U/m$^2$ |

-continued

| | |
|---|---|
| 2-(4-Hydroxy-3,5-dimethoxyphenyl)-4-<br>[4-(dimethylamino)-phenyl]-5-phenetylimidazole<br>(leuco Dye) Acetate | 0.38 g/m² |
| Bis[(vinylsulfonylmethylcarbonyl)amino]methane | 0.1 g/m² |

Then, an aqueous solution containing the following reagent was coated over the surface of the resulting reagent layer to have the following coverage. The gelatin layer was swollen and a tricot knitted cloth made by knitting PET spun yarn of 36 gage corresponding to 50 deniers and having a thickness of about 250 μm was laminated thereon under a uniform and light pressure, whereby a porous spreading layer was formed.

| | |
|---|---|
| Nonylphenoxypolyethoxyethanol<br>(containing 9 to 10 oxyethylene units on average) | 0.15 g/m² |
| Bis[(vinylsulfonylmethylcarbonyl)amino]methane | 0.4 g/m² |

Thereafter, a substrate layer was formed by applying a substrate, followed by drying, to have the following coverage, whereby a multi-layered analysis element for the quantitative analysis of α-amylase was prepared.

| | |
|---|---|
| Carboxymethylated starch | 4 g/m² |
| Nonylphenoxypolyethoxyethanol<br>(containing 9 to 10 oxyethylene units on average) | 0.15 g/m² |

The thus prepared analysis element was cut into a rectangular tip of 14 mm×13 mm, and the tip was placed in a slide frame described in Unexamined Japanese Patent Publication No. 63452/1982 to prepare a multi-layered dry slide for the analysis of α-amylase.

EXAMPLE 6

Measurement of Human Hemoglobin

Using the enzyme-labeled antibody prepared by Example 4, human hemoglobin was analyzed by a homogeneous enzyme immunoassay.

The α-amylase/Fab' bound prepared in Example 4 was diluted with saline to prepare a solution containing the bound in concentration of 0.1 mg/mL. To a 50 μl of the aliquot of diluted solution, 50 μL of saline containing a known concentration of human hemoglobin was added, followed by incubation at 37° C. for 20 minutes to proceed the immunoreaction. 50 μL of a 70 μg/mL the second antibody solution (the other IgG obtained in Example 1) in saline was added, followed by incubation at 37° C. for 5 minutes to proceed the second immunoreaction. Then, 50 μL of a 75 μg/ml solution of goat anti-mouse IgG (Fc) antibody (product of Jackson Immunoresearch) in saline was added. The resulting mixture was incubated at 37° C. for 5 minutes to proceed the third immunoreaction.

After completion of the above-described a series of immunoreactions, 10 μl of the resulting solution was spotted on the above-described α-amylase analysis slide prepared in Example 5. The slide was maintained at 37° C. and the optical density of the reflected light having a central wavelength of 650 nm was measured from the PET support side. The difference in optical density of the reflected lights measured respectively after the lapse of 3 minutes and 5 minutes were determined. A calibration curve was prepared based on the result of determination.

As Comparative Example 1, human hemoglobin was subjected to the immunoreaction in a similar manner to Example 6 except that neither the second nor the third antibody was added. As Comparative Example 2, human hemoglobin was subjected to the immunoreactions in a similar manner to Example 6 except that after the addition of the second antibody, the addition of the third antibody was omitted. Each resulting solution was used as a control. Aliquots of the resulting reaction mixtures obtained in the Comparative Examples 1 and 2 were spotted on α-amylase analysis slides and their calibration curve were drawn, as controls, respectively.

Each of the calibration curves is shown in FIG. 1. As shown in FIG. 1, inhibition of enzymatic activity by the addition of an antigen (Hb) was hardly observed when only an enzyme-labeled antibody (Ab-E) was reacted with the antigen (Hb) (FIG. 1; -●-). When the second antibody ($Ab_2$) was reacted with the reaction mixture obtained by the reaction between the antigen (Hb) and the enzyme-labeled antibody (Ab-E), the inhibition of enzymatic activity was observed with an increase in the amount of the antigen (FIG. 1; -○-). However, the inhibitory effects were not so large and the S/N ratio was not sufficient.

On the other hand, when the reaction mixture obtained by the reaction between the antigen (Hb) and the enzyme-labeled antibody (Ab-E) was reacted with the second antibody (Ab2), then with the third antibody (anti-$Ab_2$), the inhibition of enzymatic activity observed with an increase in the amount of the antigen was larger (-□-) than that of Comparative Example 2 (-○-). It was therefore confirmed that in the present Example using the third antibody, inhibition of enzymatic activity by the addition of the antigen was amplified to be larger and a sufficient S/N ratio was maintained.

EXAMPLE 7

Measurement of Human Hemoglobin Upon Use of Water-Soluble Substrate (Wet Process)

It was studied whether the suppression of enzymatic activity due to the addition of an antigen was observed when a water-soluble substrate was used as a substrate for a labeling enzyme. As the water-soluble substrate, benzylidene-p-nitrohenylmaltoheptaoside (BG7-pNP), a dye-binding oligosaccharide, was employed.

The α-amylase/Fab' bound prepared in Example 4 was diluted with saline to give its concentration of 0.1 mg/mL. To a 50 μl of the resulting diluted solution, 50 μL of saline containing a known concentration (0, 0.01, 0.1 or 1.0 μg/mL) of human hemoglobin was added, followed by incubation at 37° C. for 20 minutes. 50 μL of a 70 μg/mL solution of the second antibody (the other IgG obtained in Example 1) in saline was added, followed by incubation at 37° C. for 5 minutes. Then, 50 μL of a 75 μg/ml solution of goat anti-mouse IgG (Fc) antibody (product of Jackson Immunoresearch) in saline was added as the third antibody. The resulting mixture was incubated at 37° C. for 5 minutes.

An enzymatic substrate agent of an amylase assaying reagent ("BG7P Oriental", trade name; product of Oriental Yeast Industry) was dissolved in a buffer solution to prepare a reaction reagent solution having the following composition.

| | |
|---|---|
| BG7-pNP | 1 mM |
| Glucoamylase | 18 IU/mL |
| α-glucosidase | 10 IU/mL |
| PIPES (pH 7.0) | 0.1 M |

After preliminary heating to 37° C., 3 mL ot the reagent solution was added with 50 μL of the reaction mixture after completion of the above-described immunoreactions and a change in the absorbance per minute at a central wavelength of 450 nm was determined while maintaining the temperature at 37° C. In this reaction, the α-amylase, which was a labeling enzyme, hydrolyzed the substrate BG7-pNP, thereby forming an oligosaccharide (n=1 to 5) having not a benzylidene group but a Gn-pNP group (p-nitrophenyl group (pNP)). From the resulting oligosaccharide, p-nitrophenol (pNP) was released by the coupled reaction of glucoamylase and α-glucosidase. The p-nitrophenol thus released was quantitatively analyzed by absorbance.

As Comparative Example 3, in a similar manner to Example 7 except the immunoreaction between the enzyme-labeled antibody and the antigen was effected without adding the second and third antibodies, absorbance was measured, which was provided as a control. The results are shown in Table 1.

TABLE 1

Change in Absorbance in Example 7 and Comparative Example 3

| | Hemoglobin Concentration (μg/mL) | | | |
|---|---|---|---|---|
| | 0 | 0.01 | 0.1 | 1 |
| Comp. Ex. 3 (Ab-E) | 0.352 | 0.360 | 0.352 | 0.362 |
| Example 7 (Ab-E + Ab$_2$ + anti-Ab$_2$) | 0.359 | 0.353 | 0.361 | 0.350 |

As shown in Table 1, in each of Comparative Example 3 (control) and Example 7, variations in the enzymatic activity (change in absorbance) fell within a range of an analysis error (dispersion) even if the concentration of the antigen (Hb) was increased, indicating that in the case where the water-soluble substrate was employed, the steric hindrance against the labeling enzyme was not observed even if the second and third antibodies were reacted.

In the present invention, as described above, an antigen is reacted with an enzyme-labeled antibody, followed by the reaction with a second antibody capable of recognizing and binding to a different epitope and then with the third antibody capable of recognizing and binding to the second antibody. The enzymatic activity of the labeling enzyme is determined by a water-insoluble substrate. Accordingly, it is possible to analyze, with a sufficient S/N ratio and good sensitivity, an antigen of an intermediate molecular weight which so far exhibited no steric-hindrance-induced inhibition against enzymatic activity even bound to an enzyme-labeled antibody.

What is claimed is:

1. A homogeneous enzyme immunoassay process for measuring a concentration of an antigen by determining the change in enzymatic activity caused by a reaction between said antigen and an enzyme-labeled antibody, said process comprising:

providing an enzyme-labeled antibody comprising a conjugate of a labeling enzyme and a first monoclonal antibody;

contacting said antigen with said enzyme-labeled antibody to obtain a first reaction mixture, said enzyme-labeled antibody recognizing and binding to a first epitope of the antigen;

contacting said first reaction mixture with a second monoclonal antibody to obtain a second reaction mixture, said second monoclonal antibody recognizing and binding to a second epitope of said antigen different from the first epitope;

contacting said second reaction mixture with a third antibody to obtain a third reaction mixture, said third antibody recognizing and binding to said second monoclonal antibody;

contacting said third reaction mixture with a water-insoluble substrate; and measuring the change in activity of the enzyme after it has acted on said substrate, and relating the change in the activity of the enzyme to the concentration of the antigen.

2. The process according to claim 1, wherein said first monoclonal antibody is a Fab fragment or a Fab' fragment.

3. The process according to claim 1, wherein said third antibody binds to the Fc region of said second monoclonal antibody.

4. The process according to claim 1, wherein:

said third reaction mixture is contacted with a dry immunoassay element comprising a substrate layer containing said water-insoluble substrate.

* * * * *